United States Patent [19]

Schreinemakers

[11] 4,226,592
[45] Oct. 7, 1980

[54] ZERO-DEGREE POSTERIOR TEETH FOR A LOWER AND AN UPPER DENTURE

[75] Inventor: Josephus Schreinemakers, Maarheeze, Netherlands

[73] Assignee: Dental Holding N.V., Willemstad, Netherlands Antilles

[21] Appl. No.: 951,589

[22] Filed: Oct. 16, 1978

[30] Foreign Application Priority Data

Oct. 21, 1978 [NL] Netherlands ............... 7711568

[51] Int. Cl.³ ........................................... A61C 13/08
[52] U.S. Cl. ................................................. 433/197
[58] Field of Search ..................... 32/2, 8; 433/197

[56] References Cited

U.S. PATENT DOCUMENTS

| | | | |
|---|---|---|---|
| 1,941,735 | 1/1934 | Berry | 32/8 |
| 2,113,568 | 4/1938 | Andrus | 32/8 |
| 2,308,553 | 1/1943 | Steele et al. | 32/8 |
| 2,397,407 | 3/1946 | Butler | 32/8 |
| 2,593,815 | 4/1952 | Vidauer | 32/8 |
| 3,755,898 | 9/1973 | Wamen | 32/8 |

Primary Examiner—Robert Peshock
Attorney, Agent, or Firm—Kane, Dalsimer, Kane, Sullivan and Kurucz

[57] ABSTRACT

Zero-degree posterior teeth for a lower and an upper denture, wherein opposite posterior teeth interact at least substantially in line contact. The contour at the level of the active surface of the posterior teeth closely resembles the contour of natural posterior teeth. In each pair of opposite posterior teeth the lingual or palatal contour section of one posterior tooth is provided with a line shaped masticatory rim and the buccal contour section of this posterior tooth is provided with a masticatory plane, while the palatal or lingual contour section of the opposite posterior tooth is provided with a masticatory plane and the buccal contour section of this opposite posterior tooth is provided with a line shaped masticatory rim. The posterior teeth are provided with evacuation channels in their active surface, which channels originate near the line contact between opposite posterior teeth, their depth gradually increasing towards their end at the contour.

13 Claims, 10 Drawing Figures

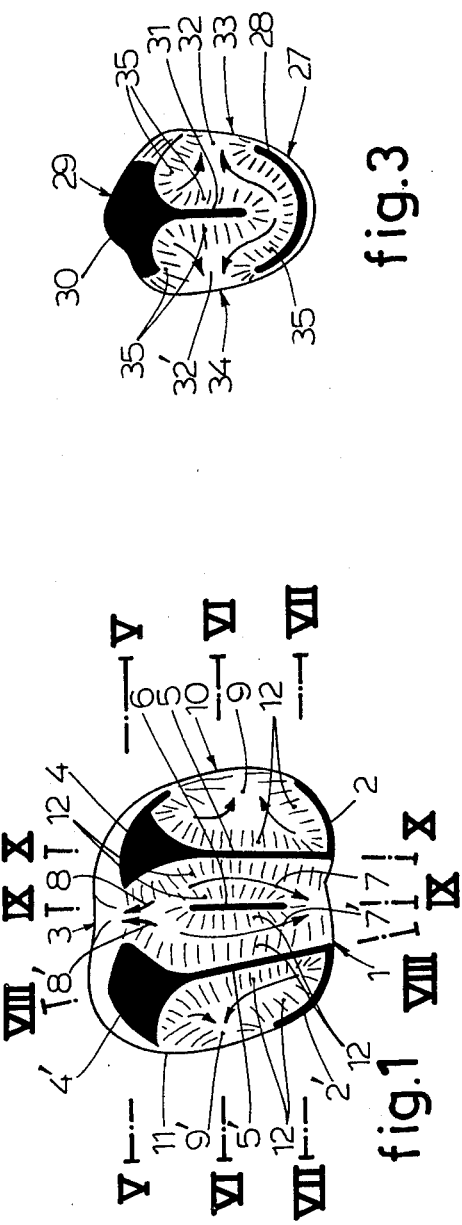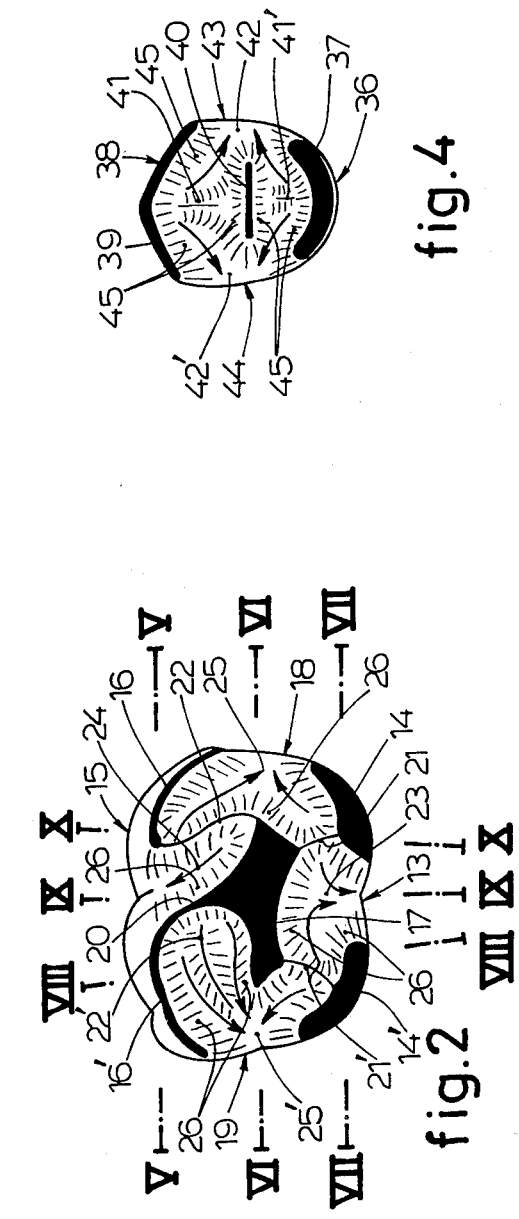

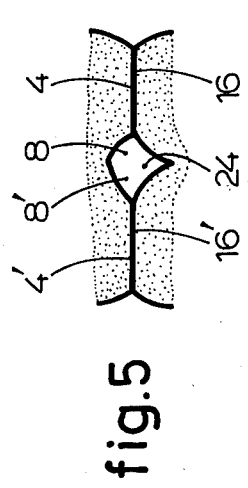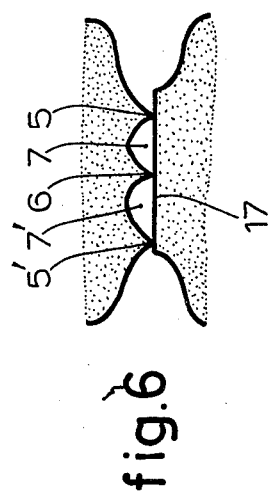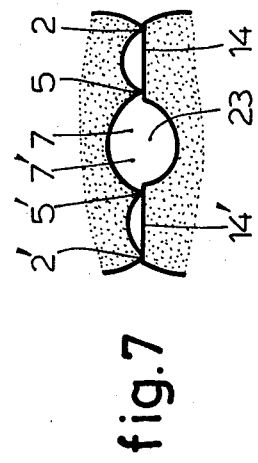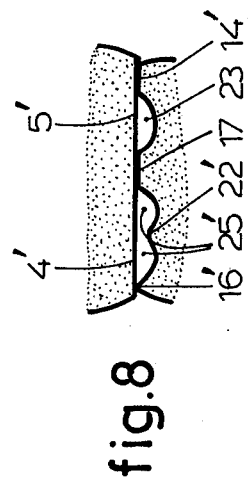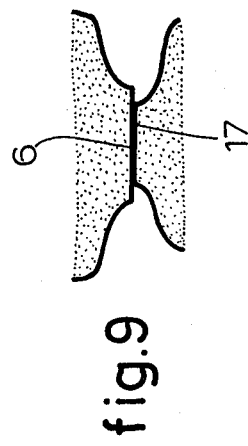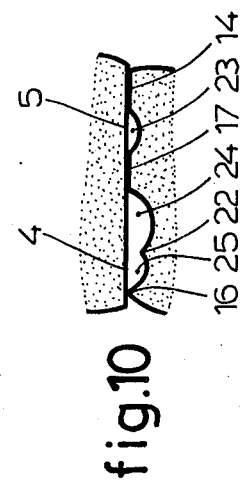

ZERO-DEGREE POSTERIOR TEETH FOR A LOWER AND AN UPPER DENTURE

BACKGROUND OF THE INVENTION

The invention relates to zero-degree posterior teeth for a lower and an upper denture, wherein opposite posterior teeth interact at least substantially in line contact.

A patient who is provided with complete dentures proves to be unable to increase the forces which he used to exert with his natural dentition for reducing the size of the food particles and for preparing the food for deglutition. Whenever the dentures cause comfortable sensations, such as pain, as frequently occurs with ill-fitting dentures, the forces for mastication will even be reduced reflectorily. With well fitting dentures the total amount of the exerted forces for mastication will generally lie within narrow limits.

Further, the tissuebed on which the dentures are seated is not intended by nature to be used as support face and thus should be relieved as much as possible, whilst nevertheless all forces which are exerted on the posterior teeth are fully transferred to this tissuebed. It is evidently of the greatest importance that the total amount of forces needed for the reduction of the size of the food particles, is reduced to a minimum, or, in other words, that the exerted forces are utilized to the utmost.

In a known embodiment of zero-degree posterior teeth for a lower and an upper denture the active surface (or end surface) of the lower posterior teeth is formed as a central mesio-distally directed, zigzag or straight, mastication ridge, which interacts with a flat active surface of the opposite upper posterior teeth.

With these known posterior teeth each pair of opposite teeth is in line contact with each other. This is based on the consideration that by reducing the contact area between the active surfaces of opposite posterior teeth, the specific surface pressure increases, which promotes the effect of mastication, i.e. the cutting of the food.

The design of the known posterior teeth as zero-degree posterior teeth—which expression means to indicate posterior teeth, each having the elements performing the cutting action lying in one flat surface (the active surface) of the posterior tooth concerned—has the advantage that the normal functional jaw movement during mastication is not obstructed in any way due to the fact that the transversal mobility is optimal. Further, the set-up of zero-degree posterior teeth in lower and upper dentures is considerably easier than the set-up of posterior cusp teeth, as the active surfaces of the zero-degree posterior teeth in the lower or upper denture are situated in one and the same flat surface.

Although the forces exerted by these known zero-degree posterior teeth for lower and upper dentures are generally efficiently utilized for the cutting of the food, these posterior teeth nevertheless show certain disadvantages.

With the known posterior teeth for lower and upper dentures the cutting action is so predominant that the contour of the active surface (the masticatory surface) of the natural posterior teeth has been abandoned completely and has been sacrificed to the cutting capacity. The extent of the contour of the known posterior teeth is significantly smaller than that of the contour of the natural posterior teeth, to such a degree that hardly a contour is left.

However, in this connection it should be considered that the mastication of food with the natural posterior teeth does not solely consist of a cutting action of the food, but should be, so to speak, a combination of cutting, pressing and mixing actions.

It is of great importance that the consumed food has a pleasant taste, not only for this fact alone, but also because in this way the stimulus for the reduction of the size of the food particles may be reflectorily raised optimally.

The pressing action intends to cause an intensive mixing of the saliva with the food and further serves to rapidly release the juices and flavors from the cells in the food, which cells are opened by the cutting action.

With the known zero-degree posterior teeth as described hereinbefore the mandatory pressing and mixing actions for preparing the food to a deglutable pulp are only obtained to a minor extent. These posterior teeth have an insufficient grip of the food because of a serious lack of active surface area. This implies that an increased tongue muscle action is required to compensate for the decreased grip of the posterior teeth on the food.

SUMMARY OF THE INVENTION

It is an object of the present invention to provide zero-degree teeth for a lower and an upper denture, which have important advantages with respect to the known posterior teeth described hereinbefore and which show considerably improved pressing and mixing actions and simultaneously a strongly intensified cutting action.

For this purpose, according to the invention the zero-degree posterior teeth for a lower and an upper denture are characterized by a combination of the following measures:

(a) the contour at the level of the active surface of the posterior teeth closely resembles the contour of natural posterior teeth;

(b) in each pair of opposite posterior teeth the lingual or palatal contour section of one posterior tooth is provided with a line shaped masticatory rim and the buccal contour section of this posterior tooth is provided with a masticatory plane, while the palatal or lingual contour section of the opposite posterior tooth is provided with a masticatory plane and the buccal contour section of this opposite posterior tooth is provided with a line shaped masticatory rim; and (c) the posterior teeth are provided with evacuation channels in their active surface, which channels originate near the line contact between opposite posterior teeth, their depth gradually increasing towards their end at the contour.

Due to the fact that according to the invention the contour of the posterior teeth at the level of the active surface closely resembles the contour of natural teeth, a superior gripping capacity of the posterior teeth on the food is obtained. An increased grip area of the posterior teeth results in a good pressing action during mastication, causing a ready and intense mixing of the flavors released from the feed and of the saliva with the alimentary pulp. Further an accelerated and intensified contact between the flavors and the taste buds on the tongue will be obtained. This enhances the enjoyment of eating and again results in a reflectory stimulus for the mastication action.

The evacuation channels which originate close to the line contact between opposite posterior teeth and which end at the contour of the posterior tooth concerned, with their greatest depth at the contour of the posterior teeth, allow the food between the dental arches to flow away with a minimum resistance and prevent development of a dry gulp during the pressing action.

Due to these deep evacuation channels the cutting capacity at the site of the line contact between opposite posterior teeth is efficiently maintained, as the food adjacent the line contact can readily evacuate.

Furthermore, the intense mixing of the released flavors and the saliva with the alimentary pulp caused by the pressing action will be considerably enhanced by allowing the food to evacuate in various directions.

The cutting capacity of the posterior teeth according to the invention for a lower and an upper denture is also by far superior to that of the known posterior teeth, as a line contact occurs along the lingual or palatal contour sections, as well as along the buccal contour sections.

According to a preferred embodiment of the posterior teeth according to the invention in each pair of opposite posterior teeth the central portion of one tooth is provided with at least one bucco-lingual or bucco-palatal line shaped masticatory rim, while the central portion of the opposite posterior tooth is provided with a mesio-distal masticatory plane or with a mesio-distal line shaped masticatory rim.

In this manner the cutting capacity of the posterior teeth according to the invention is still further improved.

In order to increase this cutting capacity to the optimum level, the line shaped masticatory rims and the masticatory planes along the lingual or palatal contour section and along the buccal contour section may extend over at least ⅔ of these contour sections.

According to the invention a line contact is obtained, which has at least twice the length of the line contact occurring with the known artificial posterior teeth.

BRIEF DESCRIPTION OF THE DRAWING

The invention will hereafter be elucidated with reference to the drawing, which shows embodiments of the zero-degree posterior teeth according to the invention for a lower and an upper denture by way of example.

FIG. 1 is a view from below of an embodiment of an upper molar according to the invention on an enlarged scale.

FIG. 2 is a plan view of an embodiment of a lower molar according to the invention on an enlarged scale.

FIG. 3 is a view from below of an embodiment of an upper premolar according to the invention on an enlarged scale.

FIG. 4 is a plan view of an embodiment of a lower premolar according to the invention on an enlarged scale.

FIGS. 5–10 are cross-sections along the lines V—V to X—X in FIGS. 1 and 2.

DESCRIPTION OF A PREFERRED EMBODIMENT

The drawings show several zero-degree posterior teeth according to the invention for a lower and an upper denture, by way of example. The opposite posterior teeth interact at least substantially in line contact.

At the level of the active surface of the posterior teeth according to the invention the contour closely resembles the contour of natural teeth. As a result the gripping capacity of the posterior teeth on the food is optimal.

FIG. 1 shows a left upper molar which is provided along its palatal contour section 1 with two line shaped masticatory rim portions 2 and 2′, which are situated in the active surface of the molar. The buccal contour section 3 of this molar is provided with two masticatory plane sections 4 and 4′, which are also situated in the active surface of the molar.

The upper molar is further provided in its central portion with two approximately parallel line shaped masticatory rims 5, 5′, which extend in the active surface of the molar. These masticatory rims 5 and 5′ extend from the masticatory plane section 4 or 4′ in the bucco-palatal sense to an end of the masticatory rim portion 2 or 2′.

Between these masticatory rims 5 and 5′ a central line shaped masticatory rim 6 extends in the bucco-palatal sense in the active surface of the molar. This masticatory rim 6 ends at a distance from the palatal and the buccal contour sections 1, 3. Evacuation channels 7, 7′ and 8, 8′ are formed between these masticatory rims 5, 5′ and 6 and end in the palatal contour section 1 and in the buccal contour section 3 respectively.

Additional evacuation channels 9, 9′ are formed laterally of each of the line shaped masticatory rims 5, 5′. These evacuation channels 9, 9′ end in the mesial contour section 10 and in the distal contour section 11 respectively.

All evacuation channels 7, 7′; 8, 8′; 9, 9′ originate near the line contact between opposite posterior teeth and show a gradually increasing depth towards their end at the contour of the tooth concerned. At this contour the depth will amount to at least 1 mm, but will generally be larger.

Further, the evacuation channels 7, 7′, which end in the palatal contour section 1, will have a larger cross-section at their end than the evacuation channels 8, 8′, which end in the buccal contour section 3.

The line shaped masticatory rim portions 2, 2′, the masticatory plane portions 4, 4′ and the masticatory rims 5, 5′ and 6 are at least partly defined by steep faces 12, which enclose an angle with the active surface of the tooth of more than 45° and which define the evacuation channels 7, 7′; 8, 8′ and 9, 9′.

FIG. 2 shows a left lower molar which is provided with two masticatory plane sections 14, 14′ along its lingual contour section 13. The masticatory plane sections 14, 14′ are situated in the active surface of this molar. This lower molar is provided with two line shaped masticatory rim portions 16, 16′ along its buccal contour section 15, which masticatory rim portions 16, 16′ also lie in the active surface of this molar. Further, the lower molar is provided with a masticatory plane 17 in its central portion, which masticatory plane 17 extends in the mesio-distal sense in the active surface of the molar. The masticatory plane 17 ends at a distance from the mesial contour section 18 and from the distal contour section 19. This distance is at least 1 mm, but will generally be larger. The masticatory plane 17 is connected to the masticatory rim portion 16′ by means of a line shaped masticatory rim 20, which extends in the active surface of the molar.

Ridges 21, 21′ and 22, 22′ extend at a deeper level than the active surface of the posterior tooth and partially define the evacuation channels 23 and 24, which end in the lingual contour section 13 and in the buccal contour section 15 respectively. They further partially define the evacuation channels 25, 25', which end in the mesial contour section 18 and in the distal contour section 19 respectively. These evacuation channels 23, 24, 25 and 25' are further defined by steep faces 26, which enclose an angle with the active surface of the tooth, which is larger than 45°. The faces 26 are situated at the inner side of the masticatory plane sections 14, 14' and of the line shaped masticatory rim portions 16, 16', substantially surround the masticatory plane 17 and also define the masticatory rim 20.

The evacuation channels 23, 24, 25 and 25' originate near the line contact between opposite posterior teeth and have a gradually increasing depth towards their end at the contour. This depth again amounts at this end to at least 1 mm.

The evacuation channel 23 which ends in the lingual contour section 13 has a larger cross-section at the location of its end at the contour of the posterior tooth than the evacuation channel 24, which ends in the buccal contour section 15.

The line contact between the upper molar according to FIG. 1 and the lower molar according to FIG. 2 is shown in FIGS. 5-10. The line shaped masticatory rim portions 2, 2' of the upper molar interact in line contact with the masticatory plane sections 14, 14' of the lower molar, whilst on the other hand the line shaped masticatory rim portions 16, 16' of the lower molar interact in line contact with the masticatory plane sections 4, 4' of the upper molar. Further the masticatory rims 5, 5' and 6 of the upper molar interact in line contact with the masticatory plane 17.

Additionally the cross-sections according to FIGS. 5-10 shows the shape of the evacuation channels 7, 7'; 8, 8'; 23, 24, 25 and 25'.

The upper premolar as shown in FIG. 3 is provided with a line shaped masticatory rim 28 along its palatal contour section 27. This masticatory rim 28 is situated in the active surface of this premolar. A masticatory plane 30 extends along the buccal contour section 29 of this premolar and is also situated in this active surface.

Further, this premolar is provided with a line shaped masticatory rim 31 in its central portion, which masticatory rim 31 is again situated in the active surface of the premolar. This masticatory rim 31 extends from the masticatory plane 30 in the bucco-palatal sense and ends at a distance from the masticatory rim 28.

Evacuation channels 32, 32' are formed on either side of this masticatory rim 31 and end in the mesial contour section 33 and in the distal contour section 34 respectively. The evacuation channels 32, 32' again originate near the line contact between opposite premolars and have a gradually increasing depth in the direction towards their end at the contour of the premolar concerned, which depth amounts to at least 1 mm, but will generally be larger.

The evacuation channels 32, 32' are defined by steep faces 35, at the inner side of the line shaped masticatory rim 28 and of the masticatory plane 30 and further on either side of the masticatory rim 31. These faces 35 enclose an angle with the active surface of the premolar which is larger than 45°.

FIG. 4 shows a lower premolar according to the invention, which is provided with a masticatory plane 37 along its lingual contour section 36. This masticatory plane 37 is situated in the active surface of the premolar. A line shaped masticatory rim 39 extends along the buccal contour section 38 in the active surface of the premolar.

A masticatory rim 40 extends in the central portion of this lower premolar in the mesio-distal sense in the active surface and ends on both sides at a distance from the contour of the premolar which amounts to at least 1 mm, but which will generally be larger. Two ridges 41, 41' extend in the bucco-lingual sense on either side of this masticatory rim 40 and partially define evacuation channels 42, 42', which end in the mesial contour section 43 and in the distal contour section 44 respectively. These evacuation channels 42, 42' are further defined by steep faces 45, which enclose an angle with the active surface of the posterior tooth, which is larger than 45°, and which extend at the inner side of the masticatory plane 37 and of the line shaped masticatory rim 39 and on both sides of the masticatory rim 40.

The evacuation channels 42, 42' originate near the line contact between opposite premolars and have a gradually increasing depth towards their end at the contour of the premolar. Their depth at the contour amounts to at least 1 mm, but will generally be larger.

The line shaped masticatory rim 28 of the upper premolar according to FIG. 3 interacts in line contact with the masticatory plane 37 of the lower premolar according to FIG. 4, whilst on the other hand the line shaped masticatory rim 39 of the lower premolar interacts in line contact with the masticatory plane 30 of the upper premolar. Further the masticatory rim 31 of the upper premolar and the masticatory rim 40 of the lower premolar interact in point contact.

The right molars and premolars for the upper and the lower dentures are mirror images of the left molars and premolars as shown in FIGS. 1-4.

The posterior teeth according to the invention have an excellent cutting capacity due to the fact that the mastication area of the active surface of each posterior tooth is in line contact with the mastication area of the active surface of the opposite posterior tooth over unequalled long distances, while the forces which are exerted will be divided over the total extension of the active surfaces of the posterior teeth. Further, the evacuation channels 7, 7'; 8, 8'; 9, 9'; 23; 24; 25, 25'; 32, 32' and 42, 42' in the active surfaces of the posterior teeth, which originate near the line contact between opposite teeth, will also promote the cutting capacity, in view of the fact that the food can easily evacuate from between the dental arches.

As the posterior teeth according to the invention have a contour at the level of their active surface which closely resembles the contour of natural teeth, an optimal grip of the posterior teeth on the food is obtained, which considerably enhances the pressing and mixing actions of the posterior teeth.

The evacuation channels are also of great importance for this mixing action. As already elucidated hereinbefore, the introduction of many directions of flow in these evacuation channels, largely stimulates the mixing of the released flavours and of the saliva with the alimentary pulp.

With the molars the larger part of the flowing alimentary pulp evacuates lingually through the evacuation channels 7, 7'; 23, while a smaller portion of the alimentary pulp evacuates through the evacuation channels 8, 8'; 24 in the direction of the vestibulum. For this reason the cross-section of the evacuation channels 7, 7'; 23 is larger than that of the evacuation channels 8, 8'; 24.

The portion of the alimentary pulp, which evacuates towards the vestibulum will again be returned between the dental arches due to the contraction of the buccinator muscle.

The portion of the alimentary pulp which evacuates lingually, will not automatically be returned by the tongue between the dental arches. The tongue has a highly selective capacity and is able to screen the components of the alimentary pulp and to decide on the necessity of additional mastication.

In dependence on the results of this screening the tongue will either selectively move the food towards the dental arches again or will have this food swallowed.

The evacuation of the alimentary pulp in the distal and mesial directions will cause an intensive mixing due to the opposite directions of flow at adjacent posterior teeth. The mesially and distally flowing alimentary pulp masses which meet in the interdental spaces have to evacuate, for which reason the mesial and distal sides of each posterior tooth have been shaped in such manner that the food can flow to the lingual side and to the buccal side. Again, the larger portion of the food will flow towards the tongue. Therefore the cross-section of the evacuation spaces in the direction of the tongue has to be at least twice as large as the cross-section of the evacuation spaces which are directed towards the vestibulum.

Although in the preceding description with reference to FIGS. 1-4 a specific design of the upper and the lower posterior teeth has been specified, the same may be reversed without difficulty, so that the design of the lower posterior teeth is applied for the upper posterior teeth and vice versa.

The invention is not limited to the embodiments shown in the drawing by way of example, which may be varied in different ways within the scope of the appended claims.

I claim:

1. Zero-degree posterior teeth for a lower and an upper denture, wherein opposite posterior teeth interact at least substantially in line-surface contact, wherein
   (a) the contour at the level of the active surface of the posterior teeth closely resembles the contour of natural posterior teeth;
   (b) in each pair of opposite posterior teeth the lingual or palatal contour section of one posterior tooth is provided with a line shaped masticatory rim and the buccal contour section of this posterior tooth is provided with a masticatory plane, while the palatal or lingual contour section of the opposite posterior tooth is provided with a masticatory plane and the buccal contour section of this opposite posterior tooth is provided with a line shaped masticatory rim; and
   (c) the posterior teeth are provided with evacuation channels in their active surface, which channels originate near the line contact between opposite posterior teeth, their depth gradually increasing towards their end at the contour, so that the line-surface contact at the contour is only interrupted by the ends of the evacuation channels.

2. Posterior teeth according to claim 1, wherein in each pair of opposite posterior teeth the central portion of one tooth is provided with at least one bucco-lingual or bucco-palatal line shaped masticatory rim, while the central portion of the opposite posterior tooth is provided with a mesio-distal masticatory plane or with a mesio-distal line shaped masticatory rim.

3. Posterior teeth according to claim 1, wherein the line shaped masticatory rims and the masticatory planes along the lingual or palatal contour section and along the buccal contour section extend over at least ⅔ of these contour sections.

4. Posterior teeth according to claim 1, wherein the palatal contour section of each upper posterior tooth is provided with a line shaped masticatory rim and the buccal contour section of this upper posterior tooth is provided with a masticatory plane, while the lingual contour section of each lower posterior tooth is provided with a masticatory plane and the buccal contour section of this lower posterior tooth is provided with a line shaped masticatory rim.

5. Posterior teeth according to claim 1, wherein the end of the evacuation channels located at the contour of the tooth concerned has a depth of at least 1 mm.

6. Posterior teeth according to claim 1, wherein the masticatory planes and the line shaped masticatory rims are at least partly defined by faces, which enclose an angle with the active surface, that is larger than 45°.

7. Posterior teeth according to claim 1, wherein the shapes of the mesial and the distal sides of the posterior teeth are such that evacuation spaces are formed between adjacent posterior teeth, one of these evacuation spaces being directed towards the tongue, while the other evacuation space is directed towards the vestibulum, the first mentioned evacuation space having the largest cross-section.

8. Molars according to claim 1, wherein the line shaped masticatory rim along the lingual or palatal contour section, or along the buccal contour section and the masticatory plane along the buccal contour section, or along the palatal or lingual contour section are interrupted.

9. Molars according to claim 8, wherein each upper molar or each lower molar is provided with two approximately parallel line shaped masticatory rims in the central portion, which masticatory rims extend from a section of the masticatory plane to an end of a masticatory rim portion, while between these masticatory rims a central bucco-lingual or bucco-palatal line shaped masticatory rim extends, which ends at a distance from the buccal contour section and from the lingual or palatal contour section, whilst evacuation channels extend between these masticatory rims, which end at the buccal contour section and at the lingual or palatal contour section respectively, while further evacuation channels are formed laterally of each of said parallel masticatory rims, which further evacuation channels end at the mesial contour section or at the distal contour section.

10. Molars according to claim 9, wherein each lower molar or each upper molar is provided with a mesio-distal masticatory plane in the central portion, which masticatory plane ends at a distance from the mesial contour section and from the distal contour section, said masticatory plane being connected with one of the masticatory rim portions through a line shaped masticatory rim, while evacuation channels are formed, which are partly defined by ridges that extend at a deeper level than the active surface of the molar, said evacuation channels ending at the lingual or the palatal contour section, at the buccal contour section, at the mesial contour section and at the distal contour section respectively.

11. Molars according to claim 10, wherein the evacuation channels which end at the lingual or palatal contour section have a larger cross-section at their end than the evacuation channels which end at the buccal contour section.

12. Premolars according to claim 1, wherein each upper premolar or each lower premolar is provided with a line shaped masticatory rim in its central portion which masticatory rim extends from the masticatory plane in the direction of the line shaped masticatory rim at the palatal or lingual contour section and ends at a distance from this masticatory rim, whilst evacuation channels are formed on both sides of this masticatory rim, which end in the mesial contour section and in the distal contour section respectively.

13. Premolars according to claim 12, wherein each lower premolar or each upper premolar is provided with a line shaped masticatory rim in its central portion which masticatory rim extends mesio-distally and ends on both sides at a distance from the contour of the premolar, whilst on both sides of this masticatory rim a ridge extends approximately perpendicular to this masticatory rim, which ridges lie at a deeper level than the active surface of the premolar and partly define evacuation channels which end in the mesial contour section and in the distal contour section respectively.

* * * * *

UNITED STATES PATENT AND TRADEMARK OFFICE
CERTIFICATE OF CORRECTION

PATENT NO. : 4,226,592

DATED : October 7, 1980

INVENTOR(S) : JOSEPHUS SCHREINEMAKERS

It is certified that error appears in the above—identified patent and that said Letters Patent is hereby corrected as shown below:

Column 1, line 15, "comfortable" should be --uncomfortable--;

Column 3, line 7, "gulp" should be --pulp--.

Signed and Sealed this

Tenth Day of November 1981

[SEAL]

*Attest:*

*Attesting Officer*

GERALD J. MOSSINGHOFF

*Commissioner of Patents and Trademarks*